(12) United States Patent
Maiwald et al.

(10) Patent No.: US 9,563,061 B2
(45) Date of Patent: Feb. 7, 2017

(54) DEVICE HAVING AN ARRANGEMENT OF OPTICAL ELEMENTS (71) Applicant: FORSCHUNGSVERBUND BERLIN E.V., Berlin (DE)

(72) Inventors: Martin Maiwald, Berlin (DE); Bernd Sumpf, Wildau (DE)

(73) Assignee: FORSCHUNGSVERBUND BERLIN E.V., Berlin (DE)

( * ) Notice: Subject to any disclaimer, the term of this patent is extended or adjusted under 35 U.S.C. 154(b) by 0 days.

(21) Appl. No.: 14/427,437

(22) PCT Filed: Sep. 12, 2013

(86) PCT No.: PCT/EP2013/068938
§ 371 (c)(1),
(2) Date: Mar. 11, 2015

(87) PCT Pub. No.: WO2014/041089
PCT Pub. Date: Mar. 20, 2014

(65) Prior Publication Data
US 2015/0219906 A1 Aug. 6, 2015

(30) Foreign Application Priority Data
Sep. 12, 2012 (DE) .................. 10 2012 216 164

(51) Int. Cl.
*G02B 5/18* (2006.01)
*G02B 27/10* (2006.01)
(Continued)

(52) U.S. Cl.
CPC .......... *G02B 27/1006* (2013.01); *G01J 3/427* (2013.01); *G01J 3/44* (2013.01); *G01N 21/65* (2013.01);
(Continued)

(58) Field of Classification Search
CPC ............. G02B 5/1861; G02B 27/1006; G02B 27/0172; G02B 27/1086; G02B 27/0101; G02B 5/18; G02B 5/1814; G02B 27/0905; G02B 5/20; G02B 5/1866
(Continued)

(56) References Cited

U.S. PATENT DOCUMENTS

2005/0105084 A1 5/2005 Wang et al.
2005/0128476 A1 6/2005 Zhao
(Continued)

FOREIGN PATENT DOCUMENTS

DE 102005054184 5/2007
EP 0472371 2/1992

OTHER PUBLICATIONS

International Search Report from PCT/EP2013/068938 mailed on Nov. 29, 2013.

*Primary Examiner* — Jade R Chwasz
(74) *Attorney, Agent, or Firm* — Fox Rothschild LLP (57) ABSTRACT

A device (122) is described having an arrangement of optical elements comprising excitation light sources (101, 115) for generating individual light beams (102, 116) having different wavelengths for exciting a sample in such a way that light scattered back from the sample as a result of the excitation is made available to a Raman spectroscopic analysis. The device (122) has deflection devices (103, 117) associated with the individual light beams (102, 116) for deflecting the individual light beams (102, 116) onto a common light path, wherein the common light path has a same optical system (109) for focusing the light beams (102, 116).

10 Claims, 6 Drawing Sheets

(51) Int. Cl.
    *G01J 3/44*     (2006.01)
    *G01N 21/65*     (2006.01)
    *G02B 27/14*     (2006.01)
    *G01J 3/427*     (2006.01)
    *G02B 27/09*     (2006.01)
    *G01N 21/39*     (2006.01)

(52) U.S. Cl.
    CPC ........... *G02B 27/09* (2013.01); *G02B 27/1086* (2013.01); *G02B 27/141* (2013.01); *G01J 2003/4424* (2013.01); *G01N 2021/399* (2013.01); *G01N 2201/024* (2013.01); *G01N 2201/0221* (2013.01)

(58) Field of Classification Search
    USPC ....... 359/566, 569, 572, 618, 629, 634, 363, 359/637, 639
    See application file for complete search history.

(56) References Cited

U.S. PATENT DOCUMENTS

2009/0121154 A1*   5/2009   Westphal ........... G01N 21/6458 250/484.4
2012/0099102 A1     4/2012   Bello

* cited by examiner

DEVICE HAVING AN ARRANGEMENT OF OPTICAL ELEMENTS

CROSS-REFERENCE TO RELATED APPLICATIONS

This application is a §371 National Stage of International Patent Application No. PCT/EP2013/068938, filed Sep. 12, 2013, which claims priority to and the benefit of German Patent Application No. 10 2012 216 164.3, filed Sep. 12, 2012, the contents of both of which are hereby incorporated by reference in their entirety.

TECHNICAL FIELD

The invention relates to a device having an arrangement of optical elements comprising excitation light sources. Particularly, the invention relates to a device having an arrangement of optical components comprising excitation light sources having different wavelengths for exciting a sample in such a way that light scattered back by the sample as a result of the excitation is made available to a Raman spectroscopic analysis.

BACKGROUND

As is known, chemical, physical and biological samples can be identified and analyzed by means of Raman spectroscopy. When a sample is excited with light, e.g. monochromatic laser light, a small part of the light is inelastically scattered in addition to the absorption and emission. The resulting signals characteristic for each sample are called Raman signals. They are spectrally shifted toward the excitation wavelength both to long wavelengths (Stokes range) and to shorter wavelengths (anti-Stokes range). Since, at room temperature, the intensity of the Raman signals is typically higher in the Stokes range, the Stokes range is preferably used for the identification and analysis of a sample.

Typically, as the excitation wavelength in Raman spectroscopy, laser light is used from the ultraviolet (UV) spectral range, e.g. 260 nm, up to the near infrared (NIR) spectral range, e.g. 1500 nm. The selection of the excitation wavelength is made according to the sample characteristic or the type of the application.

The cross-section for the generation of the Raman signals depends on the excitation wavelength $\lambda$, proportionally to $\lambda^{-4}$. An excitation at shorter wavelengths can therefore result in higher Raman intensities.

For special samples, excitations, especially in the ultraviolet and visual (VIS) spectral range, may result in resonance effects (Resonance Raman spectroscopy) and amplify the weak Raman signals by several orders of magnitude.

Nevertheless, fluorescence signals may be generated in addition to the Raman signals. Typically, they mask the weak Raman signals and thus make a Raman spectroscopic analysis of the sample impossible or difficult. If this characteristic of the sample is known prior to the examinations, the proper selection of the excitation wavelength, e.g. in the NIR spectral range, permits to avoid the simultaneous excitation of fluorescence signals.

Thus, the selection of the excitation wavelength determines the quality of the measured Raman spectra. Thus, particularly in the case of unknown samples, preliminary examinations are required for a proper selection of the excitation wavelength, which is then predetermined to a large extent for the optical measurement system.

The optical measurement system or the transfer optical system, i.e., the elements for exciting samples and for collecting the Raman signals of the samples for the purpose of spectral analysis are also called optodes.

A suitable optode guides the excitation light to the sample. A band-pass filter specially adapted to the excitation wavelength suppresses the interfering light emitted from the excitation source, such as for example plasma lines in gas lasers or amplified spontaneous emission (ASE) in diode lasers. Even unwanted signals from silica fibers with which the excitation light has been transported to the optode may be filtered out in this manner. These band-pass filters have only a narrow transmission curve and are selected to the excitation wavelength.

The light scattered back from the sample is collected in the collection path and imaged into a system for spectrally selective detection by a suitable optical system. For this purpose, dispersive elements for spectral separation and multichannel detectors, e.g. CCDs, are typically used.

There are several orders of magnitude between the intensity of an excitation laser and the intensity of the generated Raman signals. Overdriving or saturation of pixels of a CCD has to be avoided here because excess charges are transferred into adjacent pixels ("blooming") and may lead to artifacts in the Raman spectra. Consequently, the Raman signals have to be spectrally separated from the elastically scattered laser light in the collection path before reaching the detector. This typically takes place in spectrally selective elements, such as for example monochromators or optical filters. Long-pass filters or notch filters can be chosen for the detection of Stokes lines. These are adapted to the wavelength of the excitation light source and the spectral inspection range as well as the band-pass filter located in the excitation path.

Further optical elements, such as lenses, mirrors, filters and glass fibers, are located within the optode and are typically surrounded by a housing for protection. The laser light and the Raman signals get to the sample or back into the optode by passing through an optical window.

The examination of unknown substances, which is of interest e.g. for security-related applications in airports and border checkpoints, for medical or police-related applications, or in the private domain, is considerably complicated by the unique predefinition of the light sources, optical systems and filter sets. This is especially true for the portable devices for on-site measurements that are to be preferred for the above-mentioned applications.

In conventional arrangements of optical components for the Raman spectroscopy, the optical elements are fixedly mounted within an optode. Due to their spectral characteristics, however, the filters (band-pass filter and e.g. long-pass filter) have to be replaced for a change of the excitation wavelength. This requires a reconstruction of the optode.

Since the optical elements within an optode are adjusted and mounted to fixed positions, the distance between an excitation lens or collecting lens and the optical window of an optode may not be varied in a measurement system. This distance determines the position of the laser focus (or the collection spot) at the outside of the optode. In the case of a fixed distance, these positions cannot be adjusted to the optical characteristics of e.g. a transparent or turbid sample. Again, an expensive reconstruction of the optode is required.

In "Multi-excitation Raman spectroscopy technique for fluorescence rejection" OPTICS EXPRESS, vol. 16 no. 15, 21 Jul. 2008, McCain et al. describe a laser system having eight adjacent (782.6 nm-794.3 nm) wavelength stabilized diode lasers. Although eight different excitation wavelengths are used in this case, they are to be regarded as comparable with respect to the above-mentioned points, particularly regarding the characteristics of the Raman scattering. These wavelengths do not serve the selection of an excitation that is best for the Raman effect, but the selection of the Raman signals against the interfering fluorescence by measuring the spectra upon excitation with different wavelengths. In this method, known as "Shifted Excitation Difference Raman Spectroscopy" (SERDS), spectra are measured at only slightly different excitation wavelengths. Since, in the Raman spectra of both excitations, the Raman signals are shifted by the excitation shift, but comprise background signals of the same kind (e.g. by fluorescence), the Raman signals of the sample can be separated from the background signals (e.g. fluorescence signals) by differentiation between the spectra.

A band-pass filter was not commercially available for the range of the eight lasers. Therefore, a short-pass filter has been used to suppress the ASE in the Stokes range. A long-pass filter (F2 in FIG. 3) blocks the laser light. In this case, too, a change to an excitation wavelength which could lead to a significantly changed Raman intensity, e.g. 488 nm, would involve an adaptation of the band-pass filter and the long-pass filter and thus an expensive reconstruction of the described measurement system.

The U.S. Pat. No. 7,982,869 also addresses the application of SERDS. It describes a Raman analysis apparatus which is able to detect the presence of selected substances of interest by combining three-dimensional Bragg elements with conventional lasers and detectors, wherein the apparatus is inexpensive and manufactured in the size of few cubic meters, so that it may be used as a portable device. Particularly, a more complex Raman analysis can be effectuated by means of laser sources for two closely adjacent excitation wavelengths because the fluorescence background is independent from the excitation wavelength, whereas the spectral lines shift with the change of the excitation wavelength. In this case, the result of the Raman scattering can be collected by the same optical system, when both laser sources excite the sample sequentially. Further disclosed is a subtraction of the two excitation spectra in order to eliminate the fluorescence background, and a circuit for the analysis of the difference spectrum. However, a control, optimization or variation of the excitation wavelength(s) for the Raman signal is not disclosed.

The adjustment of the position of the excitation spot is described in the patent application US 2004/0160601 for a Raman spectroscopy arrangement having a low spectral resolution for use in portable and/or handy analysis devices. Here, the focus of the excitation beam can be adjusted by replacing an optical and mechanical component ("end cap"). But this adjustment can only be effectuated in predetermined discrete steps.

SUMMARY

The object of the present invention is to provide a device having an arrangement of optical components, which allows the implementation of more than two excitation light sources having spectrally widely spaced wavelengths for the Raman spectroscopic analysis in portable and/or handy devices without any adjustment or installation work. Additionally, the invention can also be applied to SERDS-based systems, but is not limited to such applications.

Thus, the present invention proposes a device having an arrangement of optical elements according to claim 1.

The invention comprises excitation light sources for emitting individual light beams having different wavelengths the spectral distance of which is equally spaced from each other in wavenumbers. The distance in wavenumbers is preferably greater than the typical spectral window of all sufficiently necessary Raman signals for the identification of unknown substances. The spectral window in terms of the present invention is that spectral range in which Raman signals of interest can be generated.

A particular advantage is the fact that by means of the inventive device, a Raman spectrum having a plurality of excitation light sources can be generated over a broad spectral range for unknown samples and thus a convenient wavelength can be used for the evaluation of the Raman spectrum of the possibly unknown samples. In particular, it is advantageous that no moving optical elements are necessary for switching between the wavelengths.

This object is achieved in that the device comprises a plurality of n>2 excitation light sources for emitting n excitation radiations with respectively different emissions equally spaced from each other in wavenumbers, which are guided along one of n different light paths, respectively; wherein a deflection device is associated with every light beam, which is formed on the light path for a respective first wavelength of the excitation radiation in order to deflect the respective light path onto a common light path, wherein the common light path comprises an optical system which is adapted to focus the excitation radiations onto a sample arranged outside the device. At least n−1 of the deflection devices comprise, respectively, a first transmission for wavelengths of one spectral range around the respective first wavelength, and a second transmission for respective other wavelengths, wherein the first transmission is smaller than the second transmission, respectively, and the wavelength ranges do not overlap.

Thereby, excitation radiation of different wavelengths can be focused onto the sample over a broad wavelength region, respectively, and the radiation (Raman signal) scattered back can subsequently be guided in a detector unit (preferably a spectrometer having a CCD camera). Due to the selected transmissions of the deflection device, it is possible to efficiently eliminate the excitation radiation from the optical collection path which can be directed to the detector unit, but to let pass the Raman radiation (particularly preferably the Stokes bands) that is spectrally close to the wavelengths of the excitation radiations, respectively, through all of the deflection devices along the optical collection path. Since the n excitation light sources are equally spaced from each other, the spectrum of interest for excitation wavelengths from different spectral ranges can be detected in a particular efficient manner.

Preferably, the Raman signal scattered at the sample is collected by the optical system and directed onto the common light path in the opposite direction.

Preferably, the reflection of the at least n−1 deflection devices for the respective first wavelength is greater than, 0.5, more preferably greater than 0.6, still more preferably greater than 0.7, still more preferably greater than 0.8, and still more preferably greater than 0.9.

Preferably, respectively, an amount of a difference between wavelengths of excitation radiations adjacent to each other in the spectrum is greater than a sum of band widths of the respective excitation radiations adjacent to each other. Here, the bandwidth refers to that bandwidth interval around the respective first wavelength (central wavelength having the highest intensity) in which lie preferably 90%, more preferably 95%, and still more preferably 99% of the energy of the excitation radiation.

The distance in wavenumbers between excitation radiations adjacent to each other in the spectrum is preferably at least 10 cm$^{-1}$, more preferably about at least 1000 cm$^{-1}$, and still more preferably about at least 2000 cm$^{-1}$.

Preferably, the at most one remaining deflection device, too, comprises a first transmission for wavelengths of a wavelength range around a first wavelength of the excitation radiation on the light path associated with the remaining deflection device, and a second transmission for respective other wavelengths, wherein the second transmission of the second deflection device is greater than the first transmission of the at most one remaining deflection device.

Preferably, the first deflection device and/or the second deflection device are formed as a notch filter or as a volume Bragg grating.

Preferably, the second transmission of the first deflection device, the second transmission of the deflection devices is respectively greater than 0.5, more preferably greater than 0.6, still more preferably greater than 0.7, still more preferably greater than 0.8, and still more preferably greater than 0.9.

The so selected transmission ratios ensure that the radiation elastically scattered back at the sample is directed with wavelengths of the respective excitation light sources by the deflection devices from the collection path, wherein the radiation inelastically scattered back at the sample (regardless of which excitation light source) may pass all of the deflection devices and thus may be made available to the detection. Thus, Raman spectra of different excitation wavelengths (excitation light sources) can be directed simultaneously or in a chronologic sequence onto one and the same detector for examination, without having to move optical elements.

The width of the edges of low transmissions of the deflection devices is limited downwards by the respective band width of the excitation light sources. A sufficient distance between the wavelengths of the respective excitation light sources should be selected in such a way that within the selected spectral inspection range, corresponding Raman signals are not directed out of the collection path by a deflection device of an adjacent wavelength (with respect to the excitation light source).

In a preferred embodiment variant, the device according to the invention is used as an optode for a device for detecting a Raman spectrum. In a particularly preferred manner, Raman spectra are generated for each of the excitation wavelengths, and subsequently a selection of a preferred excitation wavelength is made with which then the actual measurement of the sample is performed by means of at least one Raman spectrum.

Preferably, n is greater than 3, more preferably greater than 5, still more preferably greater than 7, and still more preferably greater than 9.

These light sources are superimposed on different light paths and associated devices for deflecting the individual light beams onto a common light path, wherein the common light path comprises the same optical system for focusing the light beams onto the object to be examined in the excitation path.

Here, the individual light sources are addressed by turning on and off the respective excitation. By selecting the suitable excitation source, the best wavelength with respect to the Raman signals can be selected. In this way, the signals which are sufficiently necessary for an analysis can also be generated for unknown substances by a measurement system, without changing components. Preferably, the selection of the best wavelength is made in such a way that a maximum intensity of the Raman signal or a maximum signal-to-noise ratio is present.

Switching between the different wavelengths of the device according to the invention is performed without any mechanically movable parts. Thus, a particularly stable and, at the same time, compact device is provided. In particular, the device according to the invention can be operated without any adjustment or installation work.

In another possible embodiment, the individual light beams are formed by beam shaping optical systems before the deflection and filtered by band-pass filters.

In another possible embodiment, beam shaping optical systems and band-pass filters are arranged on the different light paths.

It is also possible to arrange a beam shaping optical system on the common light path in such a way that each of the individual light beams can be subjected to beam shaping before the individual light beam is incident onto the respective deflection device.

In an embodiment particularly suitable for the compact construction, the excitation light sources are arranged on both sides of a further comprised optical collection system having an optical system for shaping a scattered light beam and a transfer optical system, wherein the optical collection system is adapted to collect light scattered by an object in the focus of one of the individual light beams, by means of the same optical system and by a collection light path comprising the common light path, and to provide it at an output, and wherein the different light paths are parallel to and spaced to the common light path and comprise mirrors for deflecting the individual light beams onto the notch filters arranged on the collection light path.

If a laser electrically emitting at two closely spaced wavelengths (as they are required for SERDS) is used as an excitation light source, this possibility of separating the Raman signals from the fluorescence background can be implemented for the measurement system, too.

In the case of implementing SERDS by means of a laser diode electrically emitting at two closely spaced wavelengths, this laser diode is driven alternatingly by the electric current applied to the laser diode under two different excitation conditions in order to generate alternatingly different excitation wavelengths, wherein the switching back and forth between the excitation conditions is performed preferably at a frequency greater than 0.1 Hz and preferably smaller than 1 kHz.

The spectral analysis of the electromagnetic radiation scattered by the medium to be examined may be performed, e.g., by coupling-in the scattered radiation into a spectrograph, wherein, respectively, at least one Raman spectrum is detected for the different excitation wavelengths from the scattered radiation, and one Raman spectrum of the medium to be examined is identified from the at least two detected Raman spectra of different excitation wavelengths in which the fluorescence background is eliminated by calculation. Here, it is preferred to synchronize the detection of the individual Raman spectra of different excitation wavelengths with the alternating driving of the laser diode. In this case, the detection of a Raman spectrum can be effectuated in a time period, respectively, in which the strength of the current applied to the laser diode is maintained constant.

Suppressing the fluorescence background is particularly efficiently possible if the excitation light sources are laser diodes which, respectively, can be driven under at least two different excitation conditions in order to generate excitation radiation of at least two different wavelengths.

In a possible embodiment, in addition, in the excitation path, the optical system which realizes the focusing onto the object to be measured is mounted onto a mobile holding device that is adjusted to the focal point or a focal region required for the measurement, e.g. electromechanically continuously, without exchanging the optical system.

This allows an individual adjustment of the position of the focus outside the optode to the position of the sample to be examined and its characteristics in order to obtain an optimum collection of generated Raman signals. In addition, it permits the suppression of signals outside the focus and the improved detection of spectroscopic signals in optically turbid or transparent samples or packaged samples.

According to another aspect of the present invention, a device for detecting a Raman spectrum of a medium to be examined is disclosed, which uses the device according to the invention as an optode. In this case, the optode comprises means for coupling-in the emitted excitation radiation into the medium to be examined. Further, the optode comprises means for coupling-in the radiation scattered from the medium to be examined into a spectral-optical system, wherein a data processing device is provided which is connected to the spectral-optical system. The data processing device is adapted to calculate a Raman spectrum of the medium to be examined from the at least two spectra of different excitation wavelengths detected by the spectral-optical system, in which the fluorescence background is separated by calculation. Preferably, the spectral-optical system is formed by a spectrograph having a four-channel detector, e.g. a CCD line.

It is particularly preferred that the laser diode for generating different excitation wavelengths is connected to a current source modulated by a modulator, and that the modulator alternatingly modulates the current source. Preferably, the switching back and forth is effectuated at a frequency greater than 0.1 Hz. Preferably, the device is coupled to a spectral-optical system. Preferably, a data processing device is connected to the modulator. Preferably, the detection of Raman spectra of different excitation wavelengths is synchronized with the alternating driving of the laser diode.

It is further preferred that the optical system arranged on the common light path can be driven to focus the excitation radiation onto a sample, and a distance of the optical system can be adjusted from a window (or an outer facet of the device through which the excitation radiation exits) and thus the position of the focal point or of a focal region is adjustable outside the device by driving the optical system. Thus, it is advantageously possible to adapt the beam shaping within the optode to the optical characteristics of e.g. a transparent or turbid sample in a simple manner. In a particularly preferred embodiment variant, the device according to the invention is used as an optode for a device for detecting a Raman spectrum, wherein Raman spectra are generated for each of the excitation wavelengths and for different focal depths, respectively, and subsequently a selection of a preferred excitation wavelength and a preferred focal depth is made with which then the actual measurement of the sample is effectuated by means of at least one Raman spectrum.

BRIEF DESCRIPTION OF THE DRAWINGS

Exemplary embodiments of the invention will now be explained in detail with reference to the Figures and the following description.

DETAILED DESCRIPTION

The device having an arrangement of optical elements exemplarily presented herein shows a new concept of an optode for the Raman spectroscopy with the possibility of changing the excitation wavelength over a broad spectral range, e.g. from NIR (785 nm) to UV (266 nm), and an adjustable position of the laser focus or the collection spot, without having to exchange the optical systems. This change of the excitation wavelength and the associated collection paths is effectuated without mobile parts.

Figure 1:
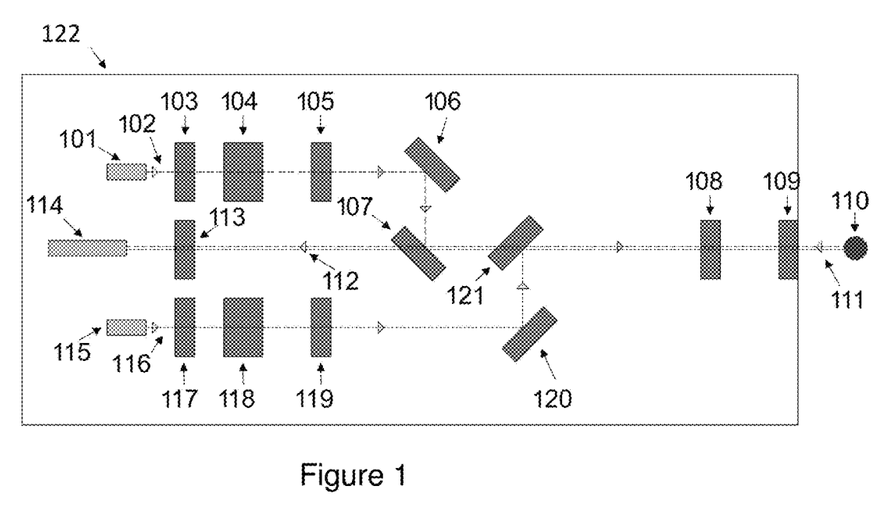
FIG. 1 shows a first exemplary optode in which the present invention is implemented.

FIG. 1 shows a first exemplary embodiment of a device having an arrangement of optical elements according to the present invention. The device 122 comprises two laser light sources 101, 115. The laser light sources 101, 115 are adapted to generate laser light beams 102, 116 having different wavelengths. Here, the generated laser light beams 102, 116 are guided on individual light paths on which optical beam shaping devices 103, 117, e.g. lenses, optical isolators 104, 118 and band-pass filters 105, 119 are arranged.

The light beams are deflected by mirrors 106, 120 onto notch filters 107, 121, wherein the notch filters 107, 121 are arranged on a common light path, so that the light beams travel a common light path after being deflected through the notch filter 107, 121. A further beam shaping optical system 108 and a window 109 are arranged on this common light path, wherein the further beam shaping optical system 108 focuses the light beams onto a focal point and thus makes available a sample 110 located in the focal point to Raman analysis. Light 111 scattered back from the sample 109 is imaged on the common light path by the window 109 and the further beam shaping optical system 108. Then the scattered light passes through the notch filters 121, 107 in the opposite direction. The notch filters block the laser light and the elastically scattered part of the scattered light. The Raman signals pass the notch filter and reach another beam shaping optical system 113. This system focuses and couples the Raman photons into a transfer optical system, e.g. a glass fiber, which transports the Raman signals to an analysis unit, e.g. a spectrometer including a four-channel detector, such as a CCD.

Volume Bragg gratings may be used instead of the mirrors 106, 120. In addition or alternatively, the notch filters 107, 121, too, may be replaced by volume Bragg gratings.

Figure 2:
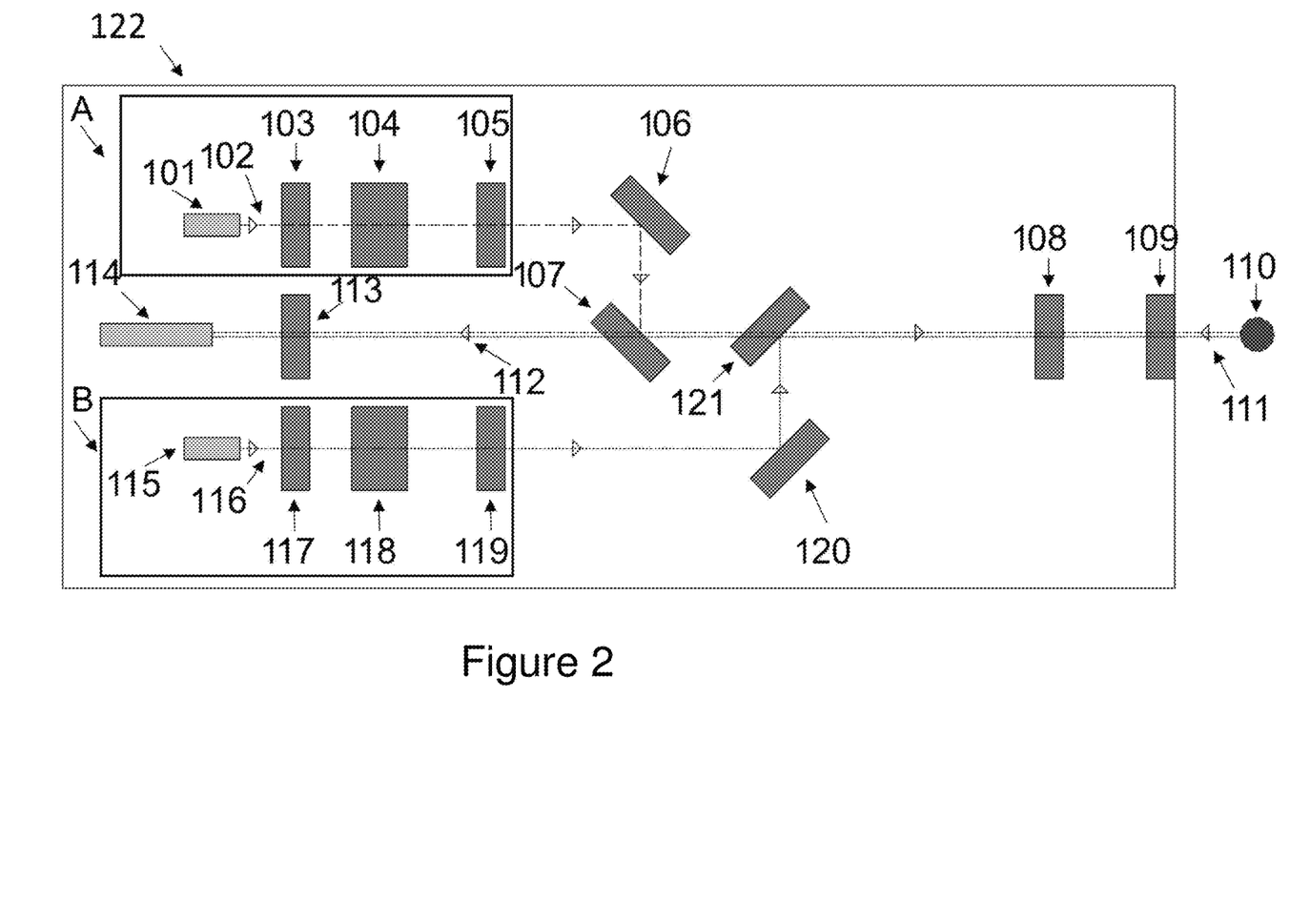
FIG. 2 shows a second exemplary optode in which the present invention is implemented.

FIG. 2 illustrates another embodiment of the inventive embodiment shown in FIG. 1. In this embodiment shown in FIG. 2, the laser sources 101, 115, the associated optical beam shaping devices 103, 117, the associated optical isolators 104, 118 and the associated optical band-pass filters 105, 119 are arranged in modules A, B which are identical with respect to the mechanical structure, except for the laser wavelength of the laser light sources 101 and 115.

Figure 3:
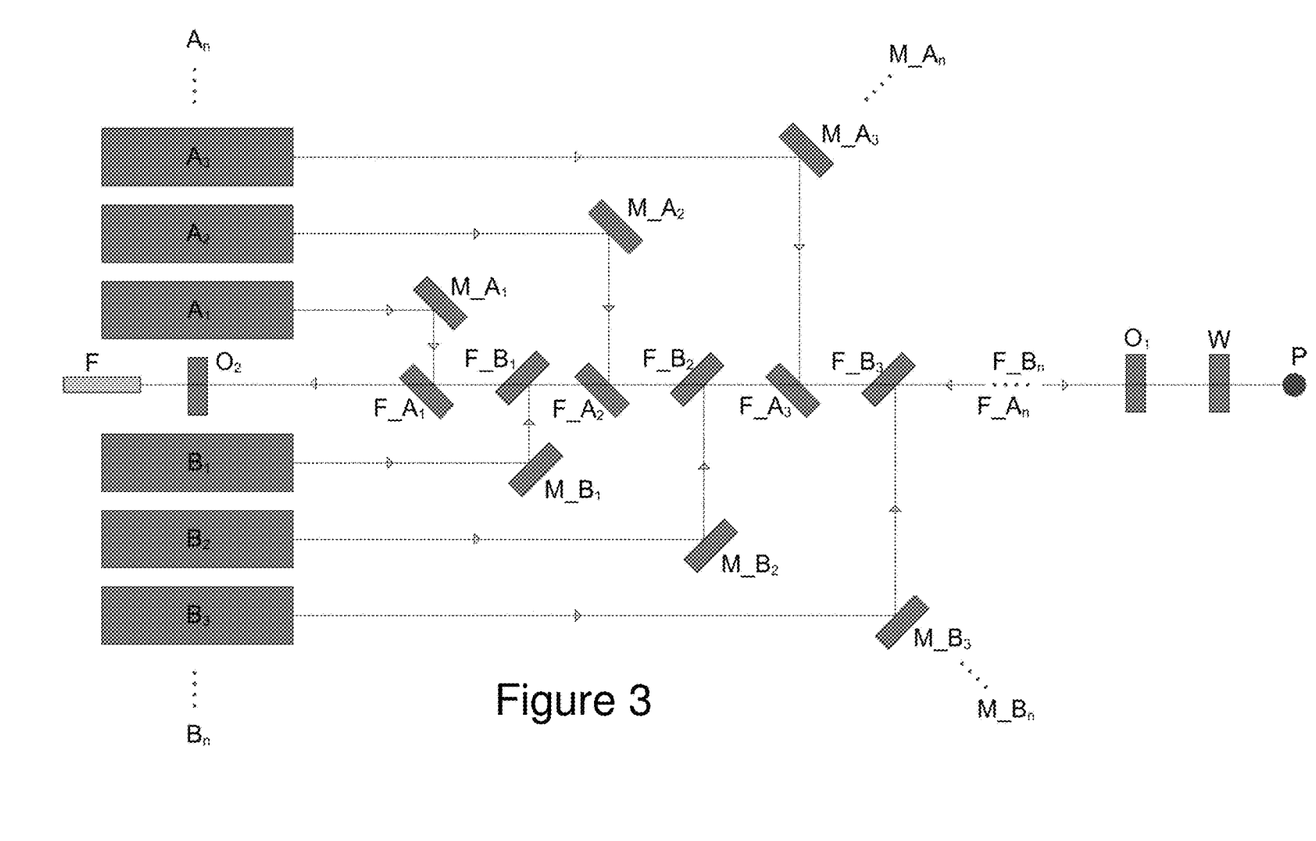
FIG. 3 shows a third exemplary optode in which the present invention is implemented.

In FIG. 3, the optode according to an exemplary embodiment of the invention is extended to a plurality of laser light sources. The modules $A_1$ to $A_n$ and $B_1$ to $B_n$ are arranged parallel to a parallel light path and adapted to emit light of different wavelengths correspondingly on parallel light paths that are spaced from the common light path. The mirrors $M\_A_1$ to $M\_A_n$ and $M\_B_1$ to $M\_B_n$ direct the light beams at the parallel light paths onto notch filters $F\_A_1$ to $F\_A_n$ and $F\_B_1$ to $F\_B_n$. The notch filters $F\_A_1$ to $F\_A_n$ and $F\_B_1$ to $F\_B_n$ are arranged on a common light path that is arranged parallel to the individual light paths onto which the individual laser light beams have been emitted. On this common light path, the light beams deflected by the notch filters are beam-shaped by a beam shaping optical system $O_1$ and focused onto a focusing point and a focusing region by a window W. A sample P located on the focusing point or in the focusing region scatters the excitation light back through the window W and the beam shaping optical system $O_1$ (here, $O_1$ serves as the optical collection system), and the light scattered back travels the common light path in the inverse direction through the notch filters $F\_A_1$ to $F\_A_n$ and $F\_B_1$ to $F\_B_n$. The laser light and the elastically scattered light are blocked by the notch filters. The spectrally shifted Raman signals pass the notch filters and are focused onto a fiber F by another beam shaping optical system $O_2$. The Raman signals coupled in here are transported to an evaluation unit via this fiber F.

Figure 4A:
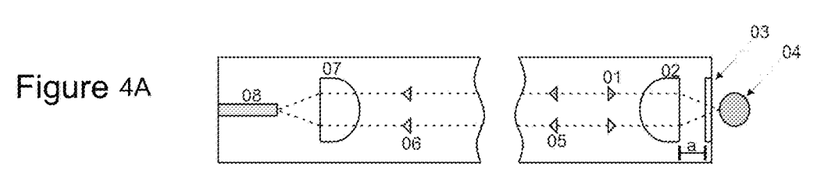
FIGS. 4A, 4B, 4C, 4D, and 4E show different configurations of sample positioning with respect to the focal length of a common optical system of an exemplary optode according to an embodiment of the invention.

FIGS. 4A to 4E show different configurations of the sample positioning with respect to the focal length of a common adjustable optical system of an exemplary optode according to an embodiment of the invention. FIG. 4A shows an excitation light 1 being focused onto a focal point or a focal region through an optical beam shaping unit 02 corresponding to the beam shaping unit 108 of FIG. 1, through a window 03 corresponding to the window 109 of FIG. 1, with a distance a between the beam shaping unit 02 and the window 03.

Figure 4B:
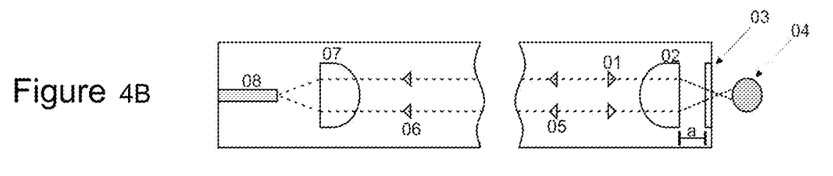
Figure 4C:
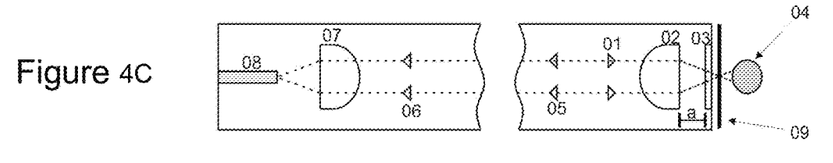
Figure 4D:
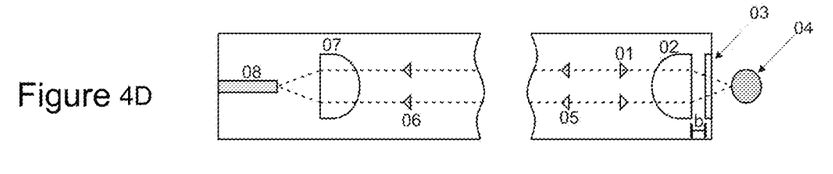
Figure 4E:
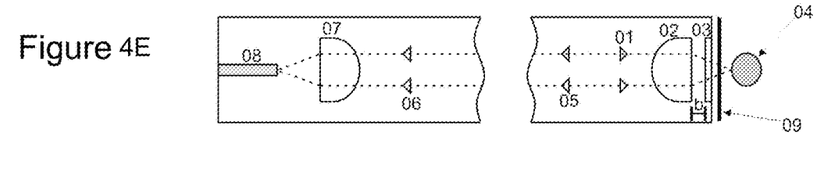

A sample 04 located in the focal point or the focal region scatters back the excitation light 01 as a light 05. The light 05 is projected onto the beam shaping device 07 corresponding to the beam shaping device 113 of FIG. 1 by the beam shaping device 02. The beam shaping device 07, in turn, focuses the light into a glass fiber 08. The case shown in FIG. 4B is analog to FIG. 4A, but now the sample 04 is no longer in the focal point, so that a maximum coupling-in of the Raman signals from the sample is no longer possible. In FIG. 4C, the extrafocal positioning of the sample 04 is effectuated as a result of an intermediate layer of a transparent or turbid material 09 arranged between the sample and the optode that leads to a shifting of the focal point. As shown in FIGS. 4D and 4E, by changing the distance between the beam shaping unit 02 and the window 03 to a length b, an object which previously was outside the focus at a focal distance of the length a or which was brought outside the focus because of a transparent or turbid intermediate layer can get back into the focus and thus made available for analysis.

Figure 5:
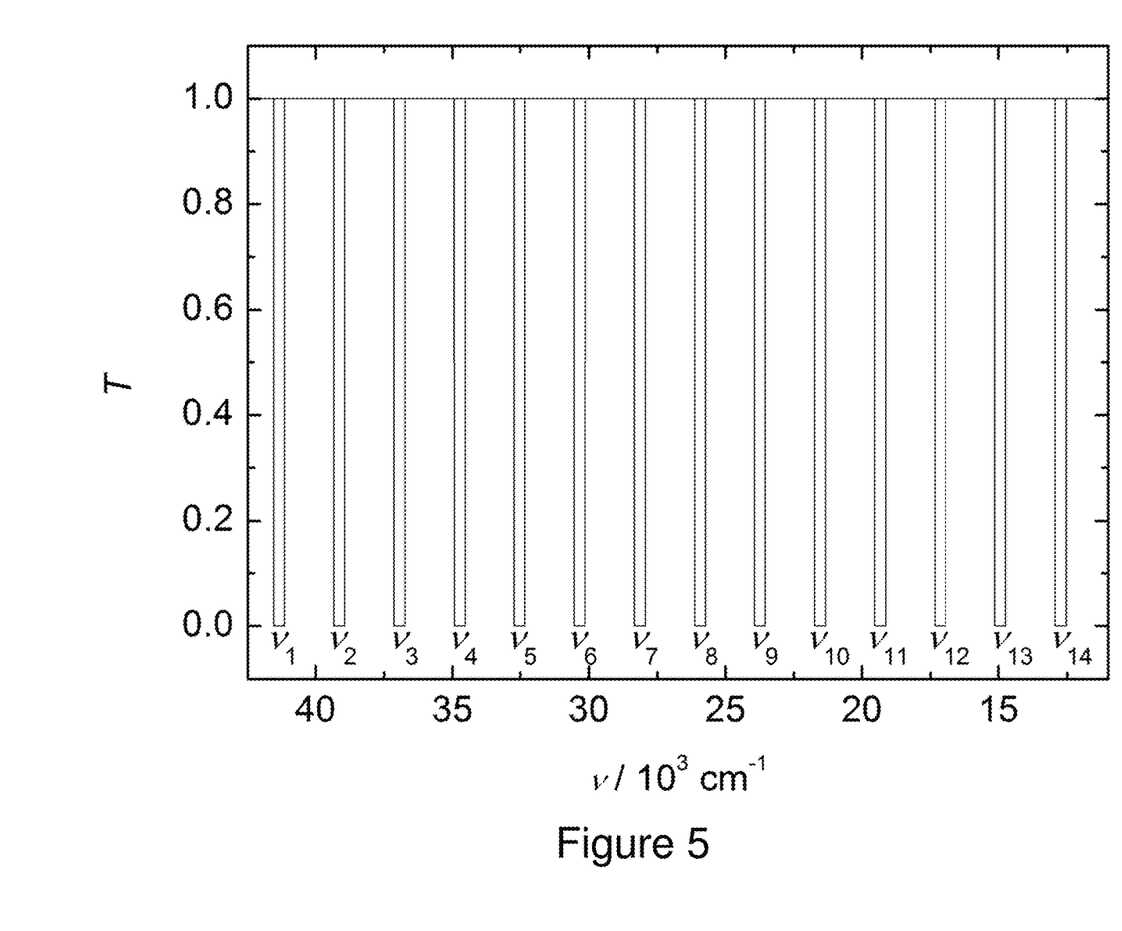
FIG. 5 shows the transmission of the plurality of deflection devices of the embodiment variant of FIG. 3 according to the wavenumber.
Figure 6:
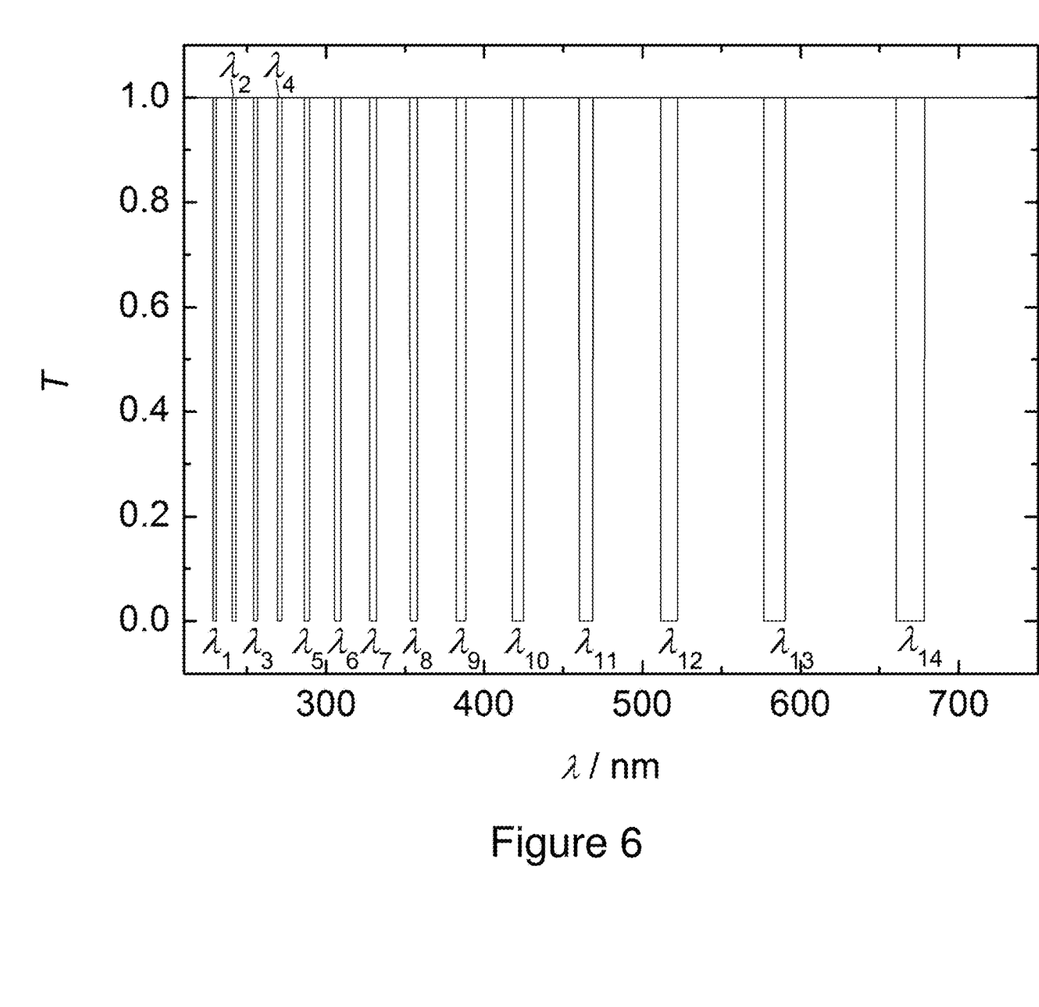
FIG. 6 shows the transmission of the plurality of deflection devices of the embodiment variant of FIG. 3 according to the wavelength.

FIGS. 5 and 6 show the transmission T of the 16 deflection devices of the preferred embodiment variant of FIG. 3 according to the absolute wavenumber (FIG. 5) or the wavelength (FIG. 6). The following wavelengths $\lambda 1$ to $\lambda 14$ were used in this case: $\lambda 1=230$ nm, $\lambda 2=242$ nm, $\lambda 3=256$ nm, $\lambda 4=271$ nm, $\lambda 5=288$ nm, $\lambda 6=307$ nm, $\lambda 7=330$ nm, $\lambda 8=355$ nm, $\lambda 9=386$ nm, $\lambda 10=421$ nm, $\lambda 11=464$ nm, $\lambda 12=517$ nm, $\lambda 13=583$ nm and $\lambda 14=669$ nm. As can be seen, Raman spectra in the range between 230 nm and 669 nm can be measured with the aid of 14 excitation light sources. Thus, Raman spectra can be generated particularly for unknown samples by the 14 excitation light sources, and a suitable selection of the excitation wavelength can be made based on the Raman spectra and the characteristics of the sample. In order to cover the spectrum, it is preferred that the central wavelengths of the excitation light sources relative to the absolute wavenumber are evenly distributed over the spectrum, that means that they are equally spaced from each other. Herein, wavenumber differences in terms of the invention are considered equal and thus the associated wavenumbers are considered equally spaced if the wavenumber differences differ by less than 5% from each other. In the case of equally spacing, the distance is for example a minimum distance. The minimum distance can be about 10 $cm^{-1}$, 1000 $cm^{-1}$ or 2000 $cm^{-1}$. The minimum distance ensures a detection window between wavenumber-adjacent excitation light sources; radiation inelastically scattered into the detection window may then be separated from elastically scattered radiation by means of the notch filters. In the case of an unevenly distribution of the central wavelengths of the excitation light sources relative to the absolute wavenumber, it is also preferred that the minimum distance between adjacent excitation light source wavenumbers is maintained. In another exemplary embodiment in which the central wavelengths are unevenly distributed, the distances between adjacent excitation light sources are equal to the minimum distance or to a multiple of the minimum distance. The width of the deflection devices preferably formed as notch filters is selected in such a way that at least 99% of the elastically scattered radiation of the excitation light sources is directed out of the collection path. The width of the edges of the 14 notch filters is kept as small as possible, so that a high transmission for the other wavelengths corresponding to the inelastic scattering of the light (Stokes range and anti-Stokes range) is provided between the notch filters.

The invention claimed is:

1. Device having an arrangement of optical elements, comprising:
a plurality of n>2 excitation light sources for emitting n excitation radiations with respectively different emissions equally spaced from each other in wavenumbers which are guided along one of a plurality of n different light paths, respectively;
wherein a deflection device is associated with every light beam, which is formed on the associated light path for a respective first wavelength of the excitation radiation in order to deflect the respective light path onto a common light path,
wherein the common light path comprises an optical system which is adapted to focus the excitation radiations
wherein at least n−1 of the deflection devices comprise, respectively, a first transmission for wavelengths of one respective spectral range around the respective first wavelength, and a second transmission for respective other wavelengths, wherein the first transmission is smaller than the second transmission, respectively, and the wavelength ranges do not overlap
wherein the at least n−1 deflection devices are formed as notch filters or volume Bragg gratings and
wherein the device further comprises an optical collection system with an optical system for shaping a scattered light beam and a transfer optical system confocally arranged with respect to the optical system, wherein the optical collection system is adapted to collect light scattered by an object in the focus of one of the individual light beams by a window and by the optical system and by a collection light path comprising the common light path, and to provide it at an output wherein the deflection devices are arranged on the collection light path.

2. Device according to claim 1, wherein, respectively, an amount of a difference between wavelengths of excitation radiations adjacent to each other in the spectrum is greater than a sum of band widths of the respective excitation radiations adjacent to each other.

3. Device according to claim 1, wherein the distance in wavenumbers between excitation radiations adjacent to each other in the spectrum is at least 10 cm-1.

4. Device according to claim 1, wherein the at most one remaining deflection device, too, comprises for wavelengths of a wavelength range around an associated first wavelength of the excitation radiation on the light path associated with the remaining deflection device, and a second transmission for associated other wavelengths, wherein the first transmission is smaller than the second transmission of the at most one remaining deflection device.

5. Device according to claim 1, wherein the first transmission of the at least n−1 deflection devices is, respectively, smaller than 0.5.

6. Device according to claim 1, wherein the second transmission of the at least n−1 deflection devices is greater than 0.5.

7. Device according to according to claim 1, wherein n is greater than 3.

8. Device according to claim 1, wherein the optical system can be driven and a distance of the optical system can be adjusted from a window and thus the position of the focal point or a focal region can be adjusted outside the device by driving the optical system.

9. Device according to claim 1, wherein beam shaping optical systems and/or band-pass filters are arranged on the different light paths.

10. Device according to claim 1, wherein the excitation light sources are laser diodes which, respectively, can be driven under at least two different excitation conditions in order to generate excitation radiation of at least two different wavelengths.

* * * * *